(12) United States Patent
Lingenhöle et al.

(10) Patent No.: US 6,786,723 B2
(45) Date of Patent: Sep. 7, 2004

(54) MEDICAL OR DENTAL-MEDICAL TREATMENT INSTRUMENT HAVING A FILTER ELEMENT

(75) Inventors: Bernhard Lingenhöle, Warthausen (DE); Thomas Braun, Biberach (DE); Anton Braun, Biberach (DE)

(73) Assignee: Kaltenbach & Voigt GmbH & Co., Biberach/Rib (DE)

( * ) Notice: Subject to any disclaimer, the term of this patent is extended or adjusted under 35 U.S.C. 154(b) by 41 days.

(21) Appl. No.: 10/080,112

(22) Filed: Feb. 21, 2002

(65) Prior Publication Data

US 2002/0115039 A1 Aug. 22, 2002

(30) Foreign Application Priority Data

Feb. 22, 2001 (DE) .......................... 101 08 565

(51) Int. Cl.[7] .......................... A61G 17/02; A61G 1/10
(52) U.S. Cl. .......................... 433/80; 433/82; 604/190
(58) Field of Search .......................... 433/80, 82, 84; 604/190

(56) References Cited

U.S. PATENT DOCUMENTS

| 4,021,353 A | * | 5/1977 | Raines et al. | |
|---|---|---|---|---|
| 4,330,274 A | | 5/1982 | Friedman et al. | |
| 4,707,262 A | * | 11/1987 | Murken | |
| 4,806,248 A | * | 2/1989 | Murken | |
| 4,894,156 A | * | 1/1990 | Murken | |
| 4,978,297 A | | 12/1990 | Vlock | |
| 5,380,201 A | * | 1/1995 | Kawata | 433/132 |
| 5,536,402 A | * | 7/1996 | Kluhsman | |
| 5,556,279 A | | 9/1996 | Wolf et al. | 433/82 |
| 5,630,939 A | * | 5/1997 | Bulard et al. | 433/92 |
| 5,716,210 A | * | 2/1998 | Novak | 433/82 |
| 5,749,726 A | * | 5/1998 | Kinsel | 433/80 |
| 5,897,317 A | * | 4/1999 | Hansen | 433/132 |
| 5,971,757 A | | 10/1999 | Selzer et al. | 433/80 |

FOREIGN PATENT DOCUMENTS

| DE | 39 06 063 C3 | 2/1989 |
|---|---|---|
| DE | 41 02 182 A1 | 1/1991 |
| EP | 0 661 024 A2 | 12/1994 |
| EP | 0 976 366 A2 | 7/1999 |
| WO | WO 99 22 663 A1 | 5/1999 |

\* cited by examiner

*Primary Examiner*—Ralph A. Lewis
(74) *Attorney, Agent, or Firm*—Marshall, Gerstein & Borun LLP

(57) ABSTRACT

The invention relates to a medical or dental-medical treatment instrument (1) having a media line, in particular for water or spray, extending from its rearward end to its forward end region, in which line an exchangeable filter element (21) is arranged. In order to reduce the flow resistance of the filter element (21), while providing a small cross-sectional size, the filter element (21) has the form of a sleeve and the direction of passage of the medium is directed transversely to the sleeve wall (21a).

13 Claims, 3 Drawing Sheets

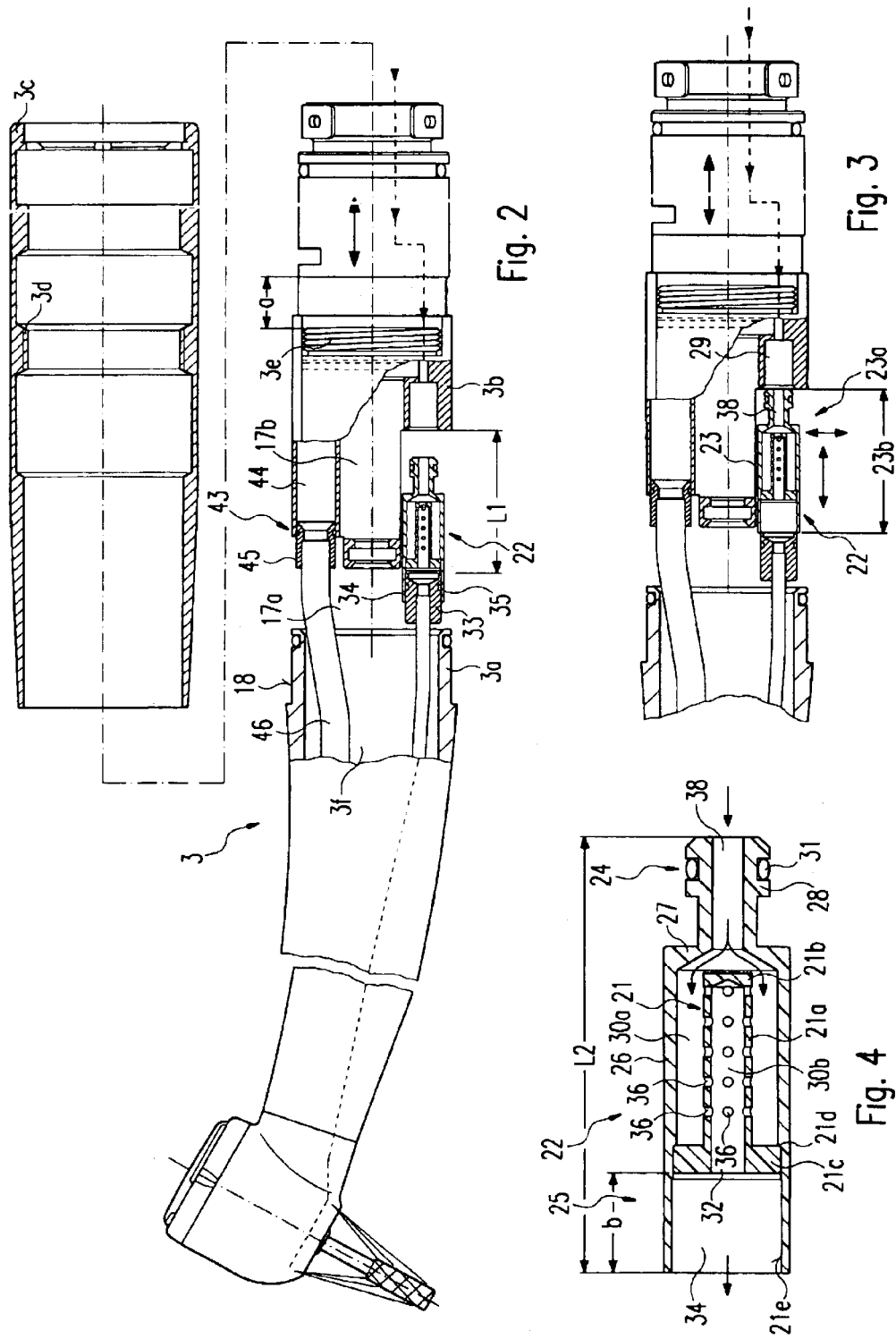

MEDICAL OR DENTAL-MEDICAL TREATMENT INSTRUMENT HAVING A FILTER ELEMENT

TECHNOLOGY FIELD

The invention relates to a medical or dental-medical treatment instrument and more particularly to a medical or dental-medical treatment instrument including a media line and an exchangeable filter.

BACKGROUND

For the kinds of treatment instruments under consideration, the structural size is restricted, in order to be able also to treat confined parts of the body, such as is the case for example in the mouth of the human body. As a consequence, media lines running in the treatment instrument are also to be formed with a cross-sectional dimension which is as small as possible. This applies also for at least one media line extending in the treatment instrument from the rear forwardly. For this reason, the media line of a treatment instrument of the kind under consideration tends to suffer a blockage in the case of contamination. This applies also if there is present in the media line a reduction of cross-section, for example in the form of a nozzle. In order to avoid such blockages it has been proposed to arrange a filter element removably in the media channel, which element can be exchanged after a certain operating time.

In U.S. Pat. No. 5,971,757 A a disc-shaped filter element is arranged in a media line between two axial parts of a treatment instrument arranged one after another.

U.S. Pat. No. 5,556,279 A shows a so-called filter cartridge for a treatment instrument of the kind under consideration, having a filter housing which is mounted between two media line sections and in which a disinfectant material is arranged between two disc-shaped filter elements, the medium flowing axially through this filter packet.

From DE 39 06 063 C2 there can be seen a dental handpiece having a filter cartridge in a water line, the handpiece consisting of three handpiece sections arranged axially one after another and the filter cartridge being arranged in the middle handpiece section.

SUMMARY OF THE INVENTION

With the configuration in accordance with the invention the filter element has the form of a sleeve, the direction of passage of the medium through the filter element being directed transversely to the sleeve wall. With this configuration a large through-flow area is available for the medium, so that the flow resistance is relatively small. By means of the sleeve form of the filter element, a small cross-sectional size is provided which allows itself to be advantageously integrated also in the restricted space relationships of a treatment instrument of the kind under consideration.

These advantages apply also for a filter cartridge and for a handpiece for a treatment instrument in accordance with the invention.

Further, with a treatment instrument formed in accordance with the invention there is provided an arrangement for mounting and dis-mounting, of the filter cartridge.

Further in accordance with the invention there is arranged in a forward handpiece part and/or an insert part which can be at least partially placed therein from the rear, a free space the lateral opening of which is covered over by means of a connecting sleeve mounted from the rear and with a retracted connecting sleeve is open, whereby a filter cartridge which can be mounted in the media line can be put in place in the free space, and again removed, through the opening. This configuration makes possible an arrangement of the filter cartridge which on the one hand is arranged internally protected from contamination and damage and on the other hand is easily accessible, for example for the purpose of cleaning or exchange.

Further developments of the solutions in accordance with the invention make possible a simple and rapid connection or release of the filter cartridge to or from associated media line sections. For this purpose, plug-in connections are preferably suited, which by means of an axial displacement of the filter cartridge and an insert part can be readily and rapidly mounted or released.

According to additional embodiments of the invention there are provided features which improve the filter cartridge both with regard to its construction and also filter characteristics and stability, and make possible a simple construction of small cross-sectional size and also an economical construction.

BRIEF DESCRIPTION OF THE DRAWINGS

Below, the invention will be described in more detail with reference to advantageous configurations of an exemplary embodiment. There is shown:

FIG. 2 the rearward part of the treatment instrument, in an intermediate mounting disposition of an insert part, partly in section;

FIG. 3 the rearward part of the treatment instrument in an intermediate mounting disposition of a filter cartridge;

FIG. 4 the filter cartridge in axial section, in an illustration to an enlarged scale;

DETAILED DESCRIPTION OF THE EMBODIMENTS

Figure 1:
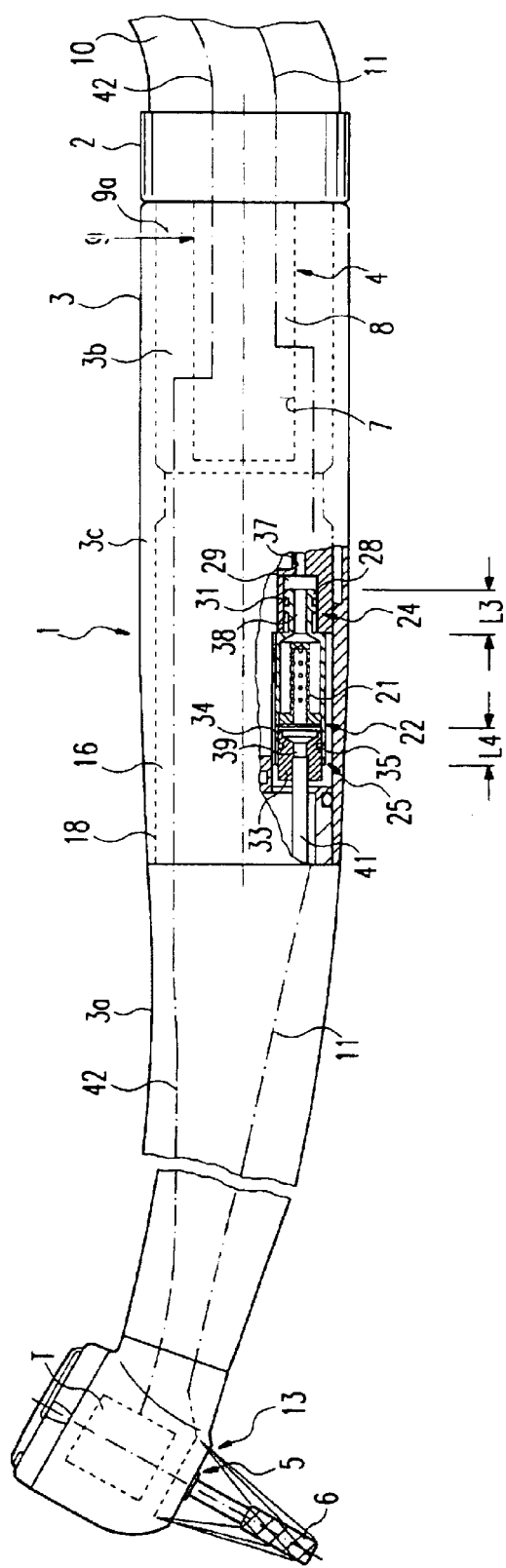
FIG. 1 a treatment instrument in accordance with the invention, in a side view.

The treatment instrument, shown in FIG. 1, designated in its entirety by 1, consists of a rearward instrument part, namely a so-called connection part 2, and a forward instrument part, namely a so-called handpiece 3, which are releasably connected with one another by means of a plug coupling 4, in particular a plug/turn coupling. With the present exemplary embodiment there is arranged at the forward end of the treatment instrument 1 a holding device 5 for a tool 6, whereby the tool 6 may project to the side or forwardly. The handpiece 3 may extend straight or be curved to the side or in an angled shape The plug/turn-coupling is formed by means of a coupling recess 7, round in cross-section, and a coupling pin 8, insertable therein with slight play for movement. With the present exemplary embodiment the coupling recess 7 is arranged at the rearward end of the handpiece 3 and the substantially cylindrical coupling pin 8 extends forwardly from the connection part 2. In the coupled condition, the coupling recess 7 and the coupling pin 8 are releasably latched to one another by means of latch device 9. This has a latch element 9a which is radially movably mounted in the one coupling part and is biased by means of a spring force into a latching disposition crossing the dividing joint, in which position the latch element engages into an annular groove in the other coupling part. Such a latching device can be overcome by means of the exercise of the manual pulling force, the latching element being self-actingly forced into its release position.

The connection part 2 is connected with a flexible supply line, which is connected with a non-illustrated control apparatus. The handpiece 3 is preferably freely rotatably mounted on the coupling pin 8, by which means handling is improved. Through the plug/turn-coupling there extends at least one media line 11 for a treatment medium, e.g. water, compressed air or a water/air mixture (spray). The media line 11 extends axially or in a Z-shape through a radial (not illustrated) or hollow cylindrical dividing joint between the coupling recess 7 and the coupling pin 8, whereby the media line 11 crosses the dividing joint in the region of an annular groove in the coupling pin 8 or in the coupling recess 7, so that in any rotational disposition the passage of media is ensured. To both sides of the passage, the dividing joint is sealed by means of a sealing ring, which may be arranged in an annular groove in the wall of the coupling recess 7 or in the outer surface of the coupling pin 8. By these means a free rotatability through 360E and more is provided. The media line 11 extends from the rearward end of the treatment instrument to its forward end region, whereby it my run in part as a channel in the instrument body or as a hose or pipeline. In the forward end region of the treatment instrument 1 the medium line 11 opens out thereof, this outlet opening 13 being directed towards the treatment site or to the tip of the tool 6.

With the present exemplary embodiment, the rearward end region of the handpiece body is formed in three parts, namely with a carrier pin 16, which projects rearwardly in one piece from the forward handpiece part 3a, which carrier pin is tapered and slotted in the longitudinal direction in the manner of a fork, an insert part 3b which can be inserted from the rear partially into the axial slot 17a of the carrier pin 16, and a connection sleeve 3c which can be mounted from the rear, surrounds the insert part 3b in the mounted disposition, fills with its forward end region a step-shaped tapering 18 in the rearward end region of the handpiece part 3a, and with an inner threaded section 3d in its middle region is screwed together with an outer threaded section 3e at the rearward fork end of the insert part 3b. The insert part 3b is of a particular constructional form which is adapted to the parts connected therewith. It is displaceable with a forward tapered web 17b into the slot 17a. In the present context it is significant that the insert part 3b, with removed connection sleeve 3c, is axially displaceable between a forward end disposition in accordance with FIG. 1 and a rearward mounting intermediate disposition in accordance with FIGS. 2 and 3, and is restricted by means of stops not illustrated in detail. The displacement length is designated by a. Further, the coupling recess 7 is arranged in the insert part 3b.

With the treatment instrument 1 in accordance with the invention there is arranged in the media line 11 a filter element 21 for filtering contaminants in the treatment medium. The filter element 21 is arranged to be exchangeable, preferably in a filter cartridge 22, the ends of which can be connected with the associated media line sections by means of plug connections 24, 25. The filter element 21 is preferably arranged in the section of the media line 11 extending in the handpiece 3, namely downstream of the plug/turn-coupling. The filter element 21 can however also be arranged in the section of the media line extending in the connection part 2. The arrangement downstream of the plug/turn-coupling is of advantage because abraded material arising through coupling and de-coupling or rotation at the coupling and sealing elements can be filtered out of the medium by the filter element 21.

With the present exemplary embodiment, the slot 17a and/or a recess 23 in the insert part 3b form a possibly common open free space 23a the length L1 of which in the pushed-out mounting intermediate disposition, with a play for movement, is dimensioned to greater then the length L2 of the filter cartridge 22, and the lateral opening of which is covered or closed by means of the pushed-on connection sleeve 3c and in its retracted position is open and accessible from the outside. The two axial ends of the filter cartridge 22 are in each case releasably connectable by means of a plug connection 24, 25, rearwardly with the insert part 3b and forwardly with the forward handpiece part 3a or a component mounted thereon. The sum of the plug-in connection lengths L3, L4 is the same as or dimensioned to be smaller then the displacement length of the insert part 3b. By these means it is possible in the mounting intermediate position of the insert part 3b, to emplace the filter cartridge 22 radially inwardly into the niche 23 and by means of a rearwardly or forwardly directed movement in the one or in the other plug connection 24, 25 to connect it with the handpiece part 3a or with the insert part 3b (FIG. 2). Upon displacement of the insert part 3b into its end position according to FIG. 1 the respective other plug connection is self-actingly and sealingly closed.

With the present exemplary embodiment, the filter cartridge 22 consists of a tube-shaped cartridge housing 26 having an end wall 27 at its rearward end, from which a cylindrical plug pin 28 projects rearwardly, with which there is associated in the insert part 3b a matching plug recess 29. By means of pushing together of these plug connection parts, the rearward plug connection 24 can be closed, it being sealed off by means of a sealing ring 31 in an annular groove, which is preferably arranged in the plug pin 28. At a spacing b, corresponding to the plug connection length L4, from the rearward end of the cartridge housing 26 the filter element 21, in the form of a sleeve, is therein coaxially so arranged and fixed that the medium flows through the preferably hollow cylindrical sleeve wall 21a radially, i.e. from the inside outwardly or from the outside inwardly. In the present exemplary embodiment the sleeve wall 21a is at one end, here at the rearward end, closed by means of an end wall 21b to a pot-like body which has a spacing from the end wall 27. The other, here forward, end of the sleeve wall 21a is attached to a disc-like filter carrier 21c which may have the form of an annular flange, the circumferential shape and size of which is adapted to the inner cross-sectional shape and size of the cartridge housing 26 and is placed therein and axially fixed e.g. by means of gluing or an press fit. For restricting the filter carrier 21c against a displacement in the cartridge housing 26 rearwardly there may be provided a shoulder surface 21d on which the filter carrier 21c bears. The inner cross-sectional size of the cartridge housing 26 may, in the end section arranged before the filter carrier 21c, be enlarged by means of an extension 21e, so that upon mounting the filter carrier 21c is readily insertable in the region of the extension 21e.

The forward plug connection 25 is formed by means of the forward end region of the inner space of the cartridge housing 26, here by means of the extension 21e, and a matching plug pin 33 on the handpiece part 3a. In the present exemplary embodiment, the plug pin 33 is attached to one or both of the forks of the handpiece part 3a bounding the slot 17, preferably formed in one piece thereon. In the axially pushed together condition of the plug pin 33 and plug recess 34, the forward plug connection 25 is closed and sealed off by means of a sealing ring 35, preferably an O-ring, in an annular groove, which is preferably arranged in the outer surface of the plug pin 33.

In the present exemplary embodiment, the filter element 21 is formed with its sleeve wall 21a in one piece on the filter carrier 21c. A two-piece configuration is, however, also possible.

At least the sleeve wall 21a is of a filter material permeable, e.g. porous, for the medium. Additionally or in place of this permeability there may be arranged in the sleeve wall 21a small through-holes 36 of which a plurality, e.g. five, are arranged one after another in the longitudinal direction and preferably of which a plurality are arranged distributed around the circumference. By these means, the filter element 21 has the structure and function of a sieve, which forms a coarse filter element and for this reason, by way of simplification is defined by means of the term filter element. That is, the filter element 21 may be of a material which is permeable or non-permeable for the medium, with or without through-holes 36 being provided With the present exemplary embodiment, the cartridge sleeve 26 and the filter element 21 formed in one piece with the filter carrier 21c, are of plastics.

In functional operation, the medium flows, after an opening of a valve in the medium line 11, e.g. associated with the control apparatus, through the supply line to the treatment instrument 1 in that it passes through a channel 37 in the plug recess 29 and through a channel 38 in the plug pin 33 into the outer hollow space 30a of the cartridge housing 26 surrounding the sleeve wall 21a and the end wall 21b, from which it flows radially inwardly through the sleeve wall 21a into an inner hollow space 30b and then through channels 32, 39 in the filter carrier 21c and in the forward plug pin 33 flows further forwardly. The channel 39 may be connected with a continuation hose 41 in the hollow chamber 3f of the handpiece part 3a, formed as a grip sleeve, in that the hose 41 is placed into the channel 39 and sealingly connected, e.g. by gluing. By reason of the sleeve shape of the filter element 21 there can be realised a relatively large through-flow region of the filter element 21, so that a relatively lesser flow resistance for the medium is provided and the pressure loss at the filter element 21 is slight. This constructional form is advantageous because with a treatment instrument 1 or handpiece 3 there is available in the longitudinal direction sufficient space, but not in the transverse direction. Since the filter element 21 can be formed small in the transverse direction, there can also be realised a small transverse dimension for the treatment instrument 1 or the handpiece 3.

After a certain operational time, for the purpose of avoiding a blockage of the filter element 21, it is advantageous to exchange it. For this purpose, the connection sleeve 3c is screwed off by means of releasing the thread engagement, the insert part 3b is displaced into its rearward mounting intermediate disposition (FIG. 2) and the filter cartridge 22 is removed, and a new filter cartridge 22 put in place, the insert part 3b displaced into its end position (FIG. 1) and the connecting sleeve 3c screwed on.

With the present exemplary embodiment, the treatment instrument 1 is a so-called turbine having a schematically indicated turbine drive T in the forward end region, which is driven by means of compressed air, which is delivered to it by means of a further medium line 42, which passes through the plug/turn coupling likewise in a Z-shape in the above described manner, and, in the connection region between the insert part 3b and the handpiece part 3a, has a plug connection 43 having a plug recess 44, here in the insert part 3b, and a plug pin 45, here e.g. on the handpiece part 3a, which upon displacement of the insert part 3b into its end position is displaceable into the plug recess 44 and sealed off by means of a sealing ring 45. This plug connection 43 is preferably so formed that it does not release even in the mounting intermediate position but remains connected, the plug pin 45 sitting at least partially in the plug recess 44 (FIG. 2). The media line section carrying on forwardly from the plug pin 45 may likewise be constituted by means of a hose 46. When the above-described forward media line sections are of sufficiently stable tubing, e.g. metal tube, the plug pin 33, 45 may be free parts, that is not connected with the handpiece part 3a, which due to their connection with the tube lines are held sufficiently stably.

Figure 5:
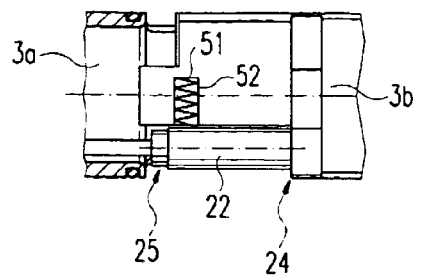
FIG. 5 the region of the treatment instrument which receives the filter cartridge, in a modified configuration.
Figure 6:
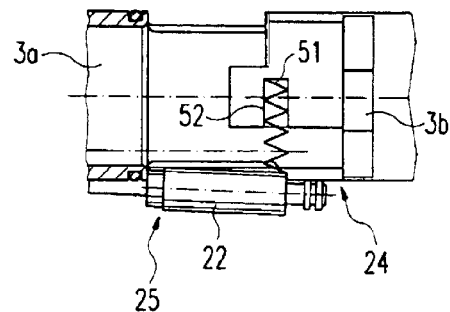
FIG. 6 the configuration according to FIG. 5 in a functional disposition of the treatment instrument in accordance with FIG. 2.

The exemplary embodiment according to FIG. 5, in which the same or similar parts are provided with the same reference signs, differs from the above-described exemplary embodiments in that in its mounted disposition the filter cartridge 22 is under a spring tensioning which biases it radially outwardly so that when the handpiece part 3a and the insert part 3b are axially drawn apart and the filter cartridge 22 is separated at one or at both plug connections 24, 25 from the handpiece part 1a and/or from the insert part 3b, the filter cartridge is displaced radially outwardly by means of the spring force, into a position in which it can be readily grasped and removed or released out of the second plug connection. For this purpose there is provided a spring 51, in particular a compression spring, which upon laterally inwards, inwardly directed placement of the filter cartridge 22 is tensioned and, after the release described above, tilts the filter cartridge laterally outwardly at least at one end, or displaces it out in the case of double-ended release. The spring 51 may be effective in the middle or in an end region of the filter cartridge 22 so that it is, under the spring tension, displaced outwardly in parallel or is tilted outwardly. In the case of the exemplary embodiment according to FIG. 5, there is provided a compression spring 51 in the form of a coil spring, which is put in place in a spring recess 52 in the insert part 3b and bears with its free end in the forward end region of the filter cartridge 22 and acts upon it permanently radially outwardly. The spring force is so great that the filter cartridge 22 is capable of displacing outwardly, but it can however cause no damage on the filter cartridge 22. Upon pulling apart of the handpiece part 3a and the insert part 3b the spring 51 can reach the middle region of the filter cartridge 22. With the exemplary embodiment according to FIGS. 5 and 6, the spring 51—through the axial pulling apart of the handpiece parts—reaches into the rearward region of the filter cartridge 22, whereby this releases from the plug receiving connection 24 and is outwardly tilted around the non-released plug-receiving connection 25. In this position the filter cartridge 22 can be readily drawn out of the plug receiving connection 25 and after a treatment or cleaning, or an exchange, can be again connected in the plug receiving connection 25. Thereafter, the filter cartridge 22 can be manually pivoted into its mounting position, whereby the spring 51 is tensioned, and the handpiece parts can be axially pushed together, whereby the plug connection 24 is closed and the mounting of the filter cartridge 22 is completed.

Figure 7:
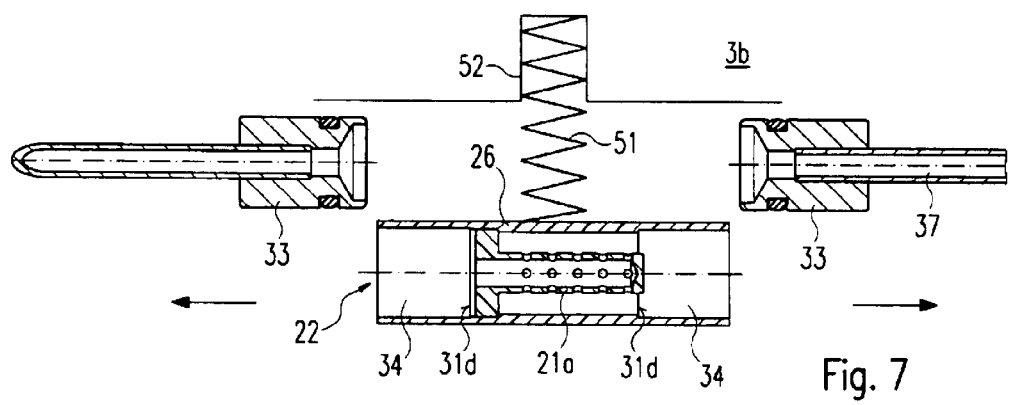
FIG. 7 the region of the treatment instrument receiving the filter cartridge in a further modified configuration, basically dismounted, and enlarged.
Figure 8:
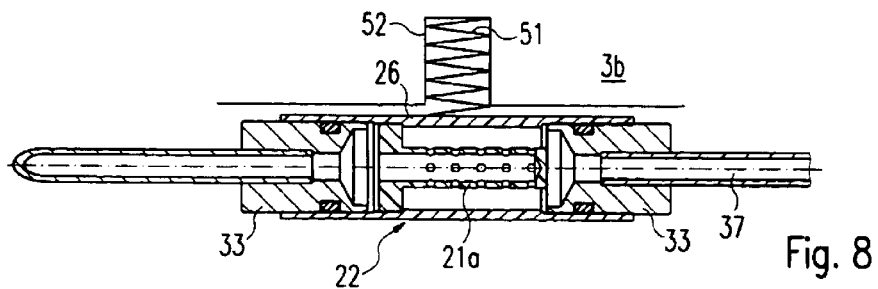
FIG. 8 the region of the treatment instrument receiving the filter cartridge, in accordance with FIG. 7, in the mounted disposition.

The exemplary embodiment according to FIGS. 7 and 8, in which the same or similar parts are likewise provided with the same reference signs, differs from the above-described exemplary embodiments in two respects.

On the one hand, the filter cartridge 22 stands under the tension of a spring 51 bearing thereon in the middle, at least in the double-ended released position. Since the filter cartridge 22 is released at both ends from the plug connection 24, 25, it can be displaced outwardly in parallel by means of the spring 51, both upon displacement outwardly upon being removed and also upon displacement inwardly upon being installed. As already described, the release and connection of the plug connections 24, 25 can also here be effected by means of the axial pulling apart and pushing together of the handpiece parts, here of the handpiece part 3a and the insert part 3b.

On the other hand, the filter cartridge 22 differs from the above-described exemplary embodiments in that it is formed at both ends in the manner of a plug connection 25. The housing of the filter cartridge or the cartridge housing 26 can, with this configuration, consist of a sleeve which has at its end towards the plug connection 24 a plug recess 34 in which a plug pin 33 can be tightly inserted, which is connected with a pipe or hose line section and is associated with the insert part 3b, as has already been described for the plug pin 33 of the plug connection 25. The insertion depth for the plug pin 33 can also be limited at this rearward end of the filter or cartridge housing 26 by means of a shoulder surface 21d.

The filter element 21 in accordance with the invention is equally well-suited also for medical or dental-medical treatment instruments 1 of other constructions and functions, e.g. for an injection or blasting handpiece or for a probe having a media delivery line, in particular a water or spray delivery line.

We claim:

1. A medical or dental-medical treatment instrument comprising:
   a media line for water or spray, extending from a rearward end to a forward end region of the treatment instrument; and
   a filter cartridge arranged in the treatment instrument in the line section of the media line, wherein the filter cartridge is provided in two-part form, including
   an exchangeable tube-shaped cartridge housing, and
   a filter element for the media line arranged in the cartridge housing,
   wherein the filter element has the form of a filter sleeve including a sleeve wall and which is closed at one end by an end wall and at the other end stands up, in the longitudinal direction of the filter cartridge, from a filter carrier in the form of an annular flange which has a through channel connected with the inner space of the filter sleeve and is either connected with a circumferential wall of the cartridge housing or inserted therein,
   wherein the direction of passage of the medium is directed transversely to the sleeve wall, and,
   wherein the filter cartridge stands under a laterally outwardly directed spring tension, which upon its dismounting displaces or tilts the filter cartridge outwardly upon pulling apart parts of the instrument.

2. Treatment instrument according to claim 1, wherein the filter cartridge is connected by plug connections with associated sections of the media line.

3. Treatment instrument according to claim 1, wherein plug connection parts are arranged at ends of the filter cartridge and include a plug pin having a through channel and a plug recess.

4. Treatment instrument according to claim 3, wherein the plug pin is smaller in its cross-sectional size than the cartridge housing and is connected with the circumferential wall of the cartridge housing by means of a housing end wall.

5. Treatment instrument according to claim 3, wherein the plug recess is formed by means of a the circumferential wall of the cartridge housing.

6. Treatment instrument according to claim 1, wherein the filter sleeve has a plurality of through-holes in a plurality of transverse planes arranged axially one behind another, and wherein each transverse plane includes a portion of the plurality of through-holes arranged distributed over a circumference of the filter sleeve.

7. Treatment instrument according to claim 1, further comprising:
   plug connection parts arranged at the ends of the filter cartridge housing and connectable or connected with associated sections of the media line.

8. Treatment instrument according to claim 7, wherein the plug connection parts are formed either at one end by a plug pin with a through channel and at the other end by a plug recess or on both ends by plug recesses.

9. Treatment instrument according to claim 8, wherein the circumferential wall of the cartridge housing projects with an end section facing away from the filter sleeve over the filter carrier and forms a plug recess.

10. Medical or dental-medical treatment instrument comprising:
    a media line for water or spray, the media line extending from a rearward end to a forward end region of the treatment instrument;
    an exchangeable filter element arranged in the media line;
    a rearward connection part;
    a forward handpiece; and
    a plug coupling releasably coupling the connection part and the forward handpiece, the plug coupling formed between the connection part and an insert part in the handpiece, which is connectable with the handpiece by a connection sleeve, which sleeve can be mounted from the rear and removed to the rear, and which insert part is, with the back connection sleeve rearwardly drawn, axially displaceable between a rearward mounting intermediate position and a forward end position, wherein, there is arranged in the forward handpiece and/or in the insert part a free space the lateral opening of which is covered over by the mounted connection sleeve and is opened with the connection sleeve drawn back, and in that a filter cartridge mountable in the media line can be put in place, and again removed, through the opening into the free space.

11. Treatment instrument according to claim 10, wherein the filter cartridge has a filter element in the form of a filter sleeve, and the direction of passage of the medium is directed transversely to the sleeve wall.

12. Treatment instrument according to claim 10, wherein the media line extends through the insert part and an up-stream plug connection is arranged between the filter cartridge and the insert part.

13. Treatment instrument according to claim 10, wherein the insert part and the connection sleeve are mounted on the handpiece in the open position.

* * * * *